(12) United States Patent
Whitmore

(10) Patent No.: US 9,168,077 B2
(45) Date of Patent: *Oct. 27, 2015

(54) SELF-DRILLING SELF-TAPPING BONE SCREW

(71) Applicant: Surgical Screw Concepts, LLC., Colfax, WA (US)

(72) Inventor: Robin C. Whitmore, Simi Valley, CA (US)

(73) Assignee: Surgical Screw Concepts, LLC., Colfax, WA (US)

(*) Notice: Subject to any disclaimer, the term of this patent is extended or adjusted under 35 U.S.C. 154(b) by 21 days.

This patent is subject to a terminal disclaimer.

(21) Appl. No.: 13/948,810

(22) Filed: Jul. 23, 2013

(65) Prior Publication Data

US 2013/0310882 A1 Nov. 21, 2013

Related U.S. Application Data

(63) Continuation of application No. 11/609,259, filed on Dec. 11, 2006, now Pat. No. 8,540,755, which is a continuation-in-part of application No. 10/624,735, filed on Jul. 21, 2003, now abandoned.

(51) Int. Cl.
*A61B 17/86* (2006.01)

(52) U.S. Cl.
CPC ............ *A61B 17/8625* (2013.01); *A61B 17/863* (2013.01); *A61B 17/8635* (2013.01)

(58) Field of Classification Search
CPC ............. A61B 17/8625; A61B 17/863; A61B 17/8635

USPC ......... 606/301, 304, 305, 307, 308, 309, 311, 606/312, 315, 316, 317, 318, 321, 65, 66, 606/286; 411/387.4, 386, 387.7, 387.8, 411/412, 413, 415, 426; 623/13.14; 29/456
See application file for complete search history.

(56) References Cited

U.S. PATENT DOCUMENTS

| 1,336,773 | A |   | 4/1920  | Caldwell            |          |
|-----------|---|---|---------|---------------------|----------|
| 3,395,603 | A | * | 8/1968  | Skierski            | 411/387.8|
| RE28,111  | E |   | 8/1974  | Laverty             |          |
| 3,861,269 | A |   | 1/1975  | Laverty             |          |
| 3,905,109 | A |   | 9/1975  | Cohen et al.        |          |
| 3,949,641 | A |   | 4/1976  | Masuda              |          |
| 4,125,050 | A |   | 11/1978 | Schwartzman et al.  |          |

(Continued)

OTHER PUBLICATIONS

U.S. Appl. No. 10/624,735, filed on Jul. 21, 2003, Robin C. Whitmore, "Self-drilling, self-tapping bone screw."

(Continued)

*Primary Examiner* — Pedro Philogene
*Assistant Examiner* — David Comstock
(74) *Attorney, Agent, or Firm* — Lee & Hayes, PLLC

(57) ABSTRACT

A self-drilling, self-tapping bone screw includes a body having a head at one end and a cutting end at an opposite end, the cutting end having a generally flat cutting surface supporting two symmetrical cutting edges which extend from the longitudinal centerline to diametrically opposed thread start points. A recess is formed in the head for receiving an end of an insertion tool. A dual lead thread extends outwardly from the body in a spiral path from the cutting end towards the head. The dual lead thread pitch is tapered towards the cutting end, and transitions to a straight or slightly tapered thread towards the head.

19 Claims, 4 Drawing Sheets

(56) References Cited

U.S. PATENT DOCUMENTS

| | | |
|---|---|---|
| 4,323,326 A | 4/1982 | Okada et al. |
| 4,730,969 A | 3/1988 | Dohi |
| 4,781,506 A | 11/1988 | Roberts et al. |
| 5,061,136 A | 10/1991 | Dixon et al. |
| 5,129,901 A | 7/1992 | Decoste |
| 5,190,426 A | 3/1993 | Wieder et al. |
| 5,356,253 A | 10/1994 | Whitesell |
| 5,435,723 A | 7/1995 | O'Brien |
| 5,597,357 A | 1/1997 | Roberts |
| 5,797,914 A | 8/1998 | Leibinger |
| 5,882,161 A | 3/1999 | Birkelbach |
| 5,925,048 A | 7/1999 | Ahmad et al. |
| 5,964,768 A | 10/1999 | Huebner |
| 5,967,783 A | 10/1999 | Ura |
| 6,129,730 A | 10/2000 | Bono et al. |
| 6,142,719 A | 11/2000 | Daubinger et al. |
| 6,235,033 B1 | 5/2001 | Brace et al. |
| 6,315,564 B1 | 11/2001 | Levisman |
| 6,328,746 B1 | 12/2001 | Gambale |
| 6,398,786 B1 | 6/2002 | Sesic |
| 6,503,252 B2 | 1/2003 | Hansson |
| 6,610,080 B2 | 8/2003 | Morgan |
| 6,620,163 B1 | 9/2003 | Michelson |
| 6,685,728 B2 | 2/2004 | Sinnott et al. |
| 6,743,233 B1 | 6/2004 | Baldwin et al. |
| 6,743,914 B2 | 6/2004 | Deng et al. |
| 2004/0044345 A1 | 3/2004 | DeMoss et al. |

OTHER PUBLICATIONS

U.S. Appl. No. 11/609,259, filed on Dec. 11, 2006, Robin C. Whitmore, "Self-drilling, self-tapping bone screw."

* cited by examiner

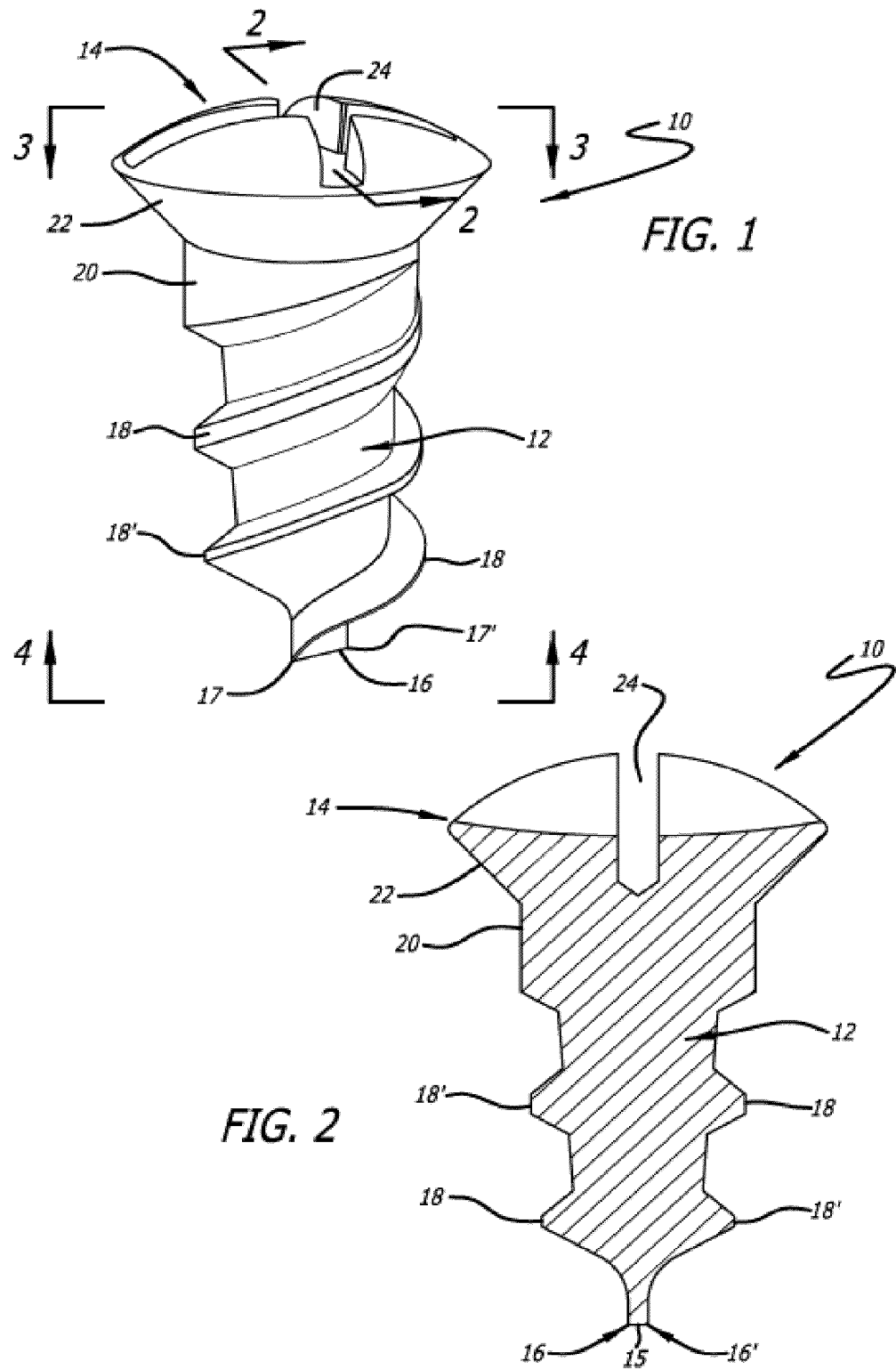

SELF-DRILLING SELF-TAPPING BONE SCREW

CROSS REFERENCE TO RELATED APPLICATION

The present application is a continuation of U.S. patent application Ser. No. 11/609,259 filed Dec. 11, 2006 which is a continuation-in-part of U.S. patent application Ser. No. 10/624,735 filed Jul. 21, 2003 both of which are incorporated by reference herein in their entirety.

FIELD OF THE INVENTION

The present invention generally relates to medical apparatuses, such as bone screws. More particularly, the present invention relates to a self-drilling, self-tapping bone screw having a dual lead thread.

BACKGROUND OF THE INVENTION

In certain surgical procedures, such as repairing fractured bones, it is necessary to attach an item, such as a plate, to a bone. For example, in repairing fractures of the facial bones or of the cranial bones, it is common to use a thin metal bone plate to hold the various pieces together. In other systems, other fasteners are used.

To use such bone plates or fasteners, holes are drilled in the various bone pieces and the bone plate or fastener is then secured to the individual bones with bone screws. Disadvantageously, this requires two steps in order to insert the screw. First, the hole must be bored in the bone. Secondly, a self-tapping bone screw is screwed into the hole. While drilling a hole significantly reduces the torque the fastener experiences during insertion, there is a significant risk that fasteners inserted with this technique establish inadequate bone/screw contact to achieve adequate connection.

Although there exists supposedly self-drilling, self-tapping fasteners and screws, it has been found that such lack adequate strength to sustain the necessary torque in such applications, or still require drilling and tapping before inserting the screw into the cranial bone.

Accordingly, there remains a need for a bone screw which can be inserted without the need for drilling or tapping. There is also a need for a bone screw which is stably inserted into the bone and which is self-drilling and self-tapping. What is further needed is a bone screw which has a very strong head to body connection so as to withstand the required torque for such insertion. The present invention fulfills these needs and provides other related advantages.

SUMMARY OF THE INVENTION

The present invention resides in a self-drilling, self-tapping bone screw. The bone screw is comprised of a durable material, such as a medical grade titanium alloy. In one embodiment, the bone screw is very small so as to be used in neurosurgery and craniofacial surgeries. As such, the bone screw is typically approximately 1.0-2.0 mm in diameter and approximately 3 to 6 mm in length.

The bone screw comprises a body having a head at one end, and a generally flat surface defining two cutting edges at an opposite end thereof. A recess is formed in the head which is configured to receive an end of an insertion tool, such as a driver bit or screwdriver.

A dual lead thread extends outwardly from the body in a spiral path from the cutting edges towards the head. The dual lead thread is typically multi-pitched. In one embodiment, the dual lead thread pitch is tapered towards the cutting edges and transitions to a straight or slightly tapered thread towards the head.

In one embodiment of the present invention, a self-drilling bone screw is provided comprising a body having a head at one end and a cutting end at an opposite end thereof, the cutting end comprising a generally flat cutting surface supporting two symmetrical cutting edges which extend from the longitudinal centerline to diametrically opposed thread start points, and a dual lead thread extending outwardly from the body in a spiral path from the cutting end towards the head.

In another embodiment, the dual lead thread is multi-pitched. In another embodiment, the dual lead thread pitch is tapered towards the cutting end and transitions to a straight or slightly tapered thread towards the head.

In one embodiment of the present invention, a self-drilling bone screw is provided comprising a body having a head at one end and cutting edge comprising a generally flat cutting surface at an opposite end thereof and a dual lead thread extending outwardly from the body in a spiral path from the cutting end towards the head, the dual lead thread being multi-pitched such that the pitch of the thread is tapered towards the cutting end and transitions to a straight or slightly tapered thread towards the head.

In yet another embodiment, the bone screw includes a recess formed in the head configured to receive an end of an insertion tool. In another embodiment, the bone screw is comprised of a medical grade titanium alloy.

In another embodiment of the present invention, the bone screw is approximately 1.0 to 2.0 mm in diameter and approximately 3.0 to 6.0 mm in length. In another embodiment, the width of the generally flat cutting surface is approximately 0.1 mm.

In one embodiment, a self-drilling, self-tapping bone screw is provided comprising a body comprised of medical grade titanium alloy of approximately 1.0 to 2.0 mm in diameter and approximately 3.0 to 6.0 mm in length, the body having a head at one end and a cutting end comprising a generally flat cutting surface at an opposite end thereof; a dual lead thread extending outwardly from the body in a spiral path from the cutting end towards the head, the dual lead thread being multi-pitched such that the pitch of the thread is tapered towards the cutting end and transitions to a straight to slightly tapered thread towards the head; and a recess formed in the head configured to receive an end of an insertion tool.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention.

FIG. 1 is a perspective view of a bone screw embodying the present Invention.

FIG. 2 is a cross-sectional view of the bone screw of the present invention taken generally along the longitudinal centerline (line 2-2 of FIG. 1).

DETAILED DESCRIPTION OF THE INVENTION

Figure 3:
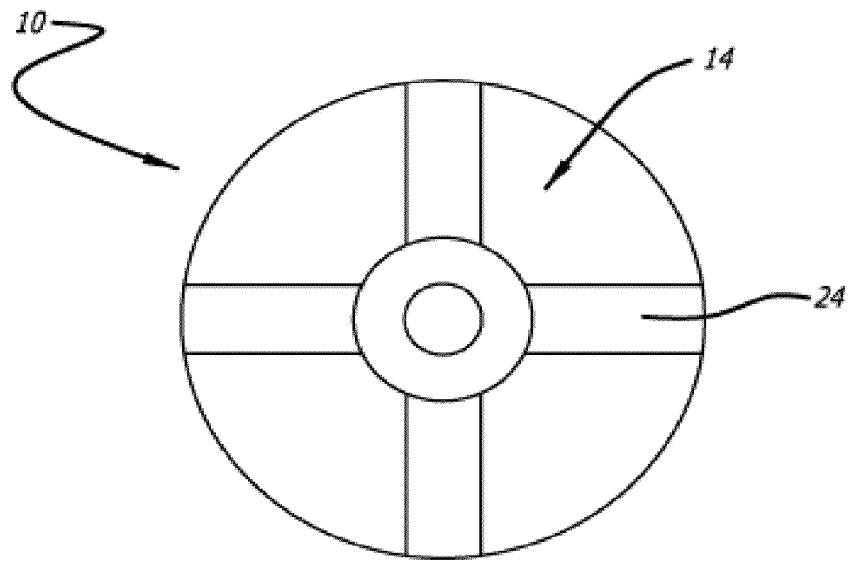
FIG. 3 is an end view of the head of the bone screw of the present invention taken generally along line 3-3 of FIG. 1.

The present invention resides in a self-drilling, self-tapping bone screw. The bone screw is comprised of a durable material, such as a medical grade titanium alloy.

As shown in the accompanying drawings, for purposes of illustration, the present invention resides in a bone screw, generally referred to by the reference number 10. The bone screw 10 is designed such that it is self-drilling or self-boring, as well as self-tapping, thus eliminating the need for drilling and tapping to insert the screw into the bone, as with prior art screws. Although not limited to such, the bone screw 10 is primarily intended for use in neurosurgery and craniofacial surgery applications.

With reference now to FIGS. 1-4, the bone screw 10 is comprised of an elongated body or shank 12 having a head 14 at one end thereof and a cutting end having symmetrical cutting edges 16 and 16' at an opposite end thereof. In the preferred neurosurgery and craniofacial surgery usage, the screw 10 is approximately 1.0 to 2.0 mm in diameter, and approximately 3.0 to 6.0 mm in length. However, the dimensions can be altered to suit the needs of the particular application, and the invention is not intended to be limited to such dimensions. For example, the diameter of the bone screw 10 of the present invention may be between 1.0 and 5.0 mm, and have a length of 3.0 to 100 mm for other medical procedures requiring bone screws of greater dimensions. The bone screw 10 is comprised of a hard and durable material, such as, but not limited to, titanium that is medically acceptable for insertion into the body, and possesses sufficient strength to withstand the torque and tension exerted upon the screw 10 during installation. Preferably, the bone screw 10 is comprised of medical grade titanium, such as TI6AL4V, or commercially pure titanium.

Figure 4:
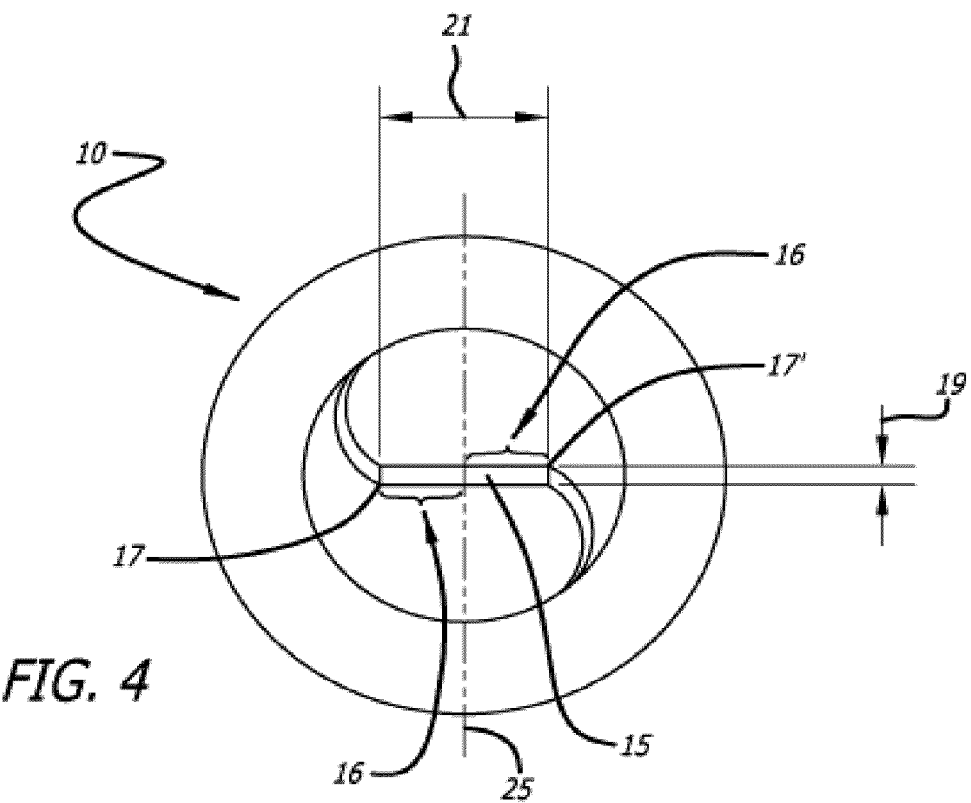
FIG. 4 is an end view of the cutting end of the bone screw of the present invention taken generally along line 4-4 of FIG. 1.

With particular reference to FIGS. 1 and 4, the symmetrical cutting edges 16 and 16' are unique, in that they lay on a generally flat surface 15 and extend from the longitudinal centerline 25 outwardly to diametrically opposed thread start points 17 and 17', creating almost instant thread forming as well as cutting an internal diameter for the thread. The majority of prior art screws are formed to a point. However, it has been found that the point promotes wobbling when the surgeon attempts to start the screw into the bone. It has been found that the flat cutting surface 15 provides a stable start into the bone. Also, the cutting edges 16 and 16' remain sharp, allowing for multiple removals and insertions of the same screw 10.

The dimensions of the generally flat cutting surface 15 are related to the diameter of the screw. As would be understood by persons of ordinary skill in the art, as the diameter of the screw 10 increases, the length and width of the flat cutting surface 15 generally will increase. In one embodiment of the present invention, the diameter of the screw is 1.5 mm, the width 19 of the generally flat cutting surface 15 is approximately 0.1 mm and the length 21 is approximately 0.5 mm. In another embodiment, a screw with a diameter of 2.0 mm has a width 19 of approximately 0.1 mm and a length 21 of approximately 0.5 mm. However, widths of more than 2.0 mm will require an increase in at least one of the length or width of the flat cutting surface 15 as compared to the 1.5 mm diameter screw.

With reference now to FIGS. 1 and 2, a dual lead thread 18 and 18' is formed on the body 12 so as to extend outwardly and form a spiral path from the cutting edges 16 and 16' towards the head 14. A double-lead or dual lead thread 18 and 18' beginning with the flat cutting surface 15 provides an easy start of the screw 10 into the bone. It has also been found that such dual lead threads 18 and 18' facilitate drilling into the bone, resulting in double the axial travel per turn. Thus, fewer turns are required to completely install the screw 10. Additionally, it has been found that the dual lead thread 18 and 18' pulls bone chips out of the hole, whereas prior art bone screws can compress the bone chips inside of the hole.

The dual lead thread 18 and 18' is multi-pitched. That is, the thread pitch is tapered towards the cutting edges 16 and 16', and transitions to a straight or slightly tapered thread towards the head 14 of the screw 10. This allows an easier start of the screw 10 into the bone, and provides secure tightening with the bone. The cutting process for forming the dual thread 18 and 18' design results in a thread pitch of 14.14 threads per inch on the cutting end, 29.32 threads per inch on the main body portion 12, and approximately 41.66 threads per inch of the pull-out portion of the screw 10 based on a 1.5 mm diameter screw. The multi-pitched thread design also provides superior strength at the head 14 to thread 18 or 18' transition 20, as illustrated in FIG. 1. This provides higher strength due to less metal removal during the manufacturing process. Thus, the screw 10 of the present invention can withstand relatively high torque.

With reference now to FIGS. 1, 2 and 3, the head 14 has a generally conical shape with an angled bevel 22 extending between the body 12 and the head 14. The angle of the bevel 22 is optimized to prevent hole-through while minimizing the head's profile. As described above, the interface 20 between the head 14 and the body 12 is specifically designed to maximize the torque it can withstand and minimize the amount of material removed in the formation of the screw 10. The head 14 includes a recess 24 which is sized and shaped such so as to accept an end of an insertion tool. As illustrated, the recess 24 is in a form of a cruciform or slot so as to accept the end of a screwdriver or driver bit. However, it should be understood that the recess 24 can comprise a slot, a hex-shaped recess, a square-shaped recess, etc. to accept the tips of different insertion tools.

The bone screw 10 of the present invention provides many advantages over comparable screws used previously. The flat cutting surface 15 promotes stability during insertion, and the cutting edges 16 and 16' remain sharp so that the screw 10 can be removed and inserted multiple times. The dual-thread design 18 and 18' enable the screw 10 to be self-drilling and self-tapping, saving time in the insertion process and providing a more secure and tight fit with the bone. A minimal amount of metal is removed during the manufacturing process so that the transition between the head 14 and the body 12 can withstand the high tension and torque exerted thereupon during the insertion and removal process.

Figure 5:
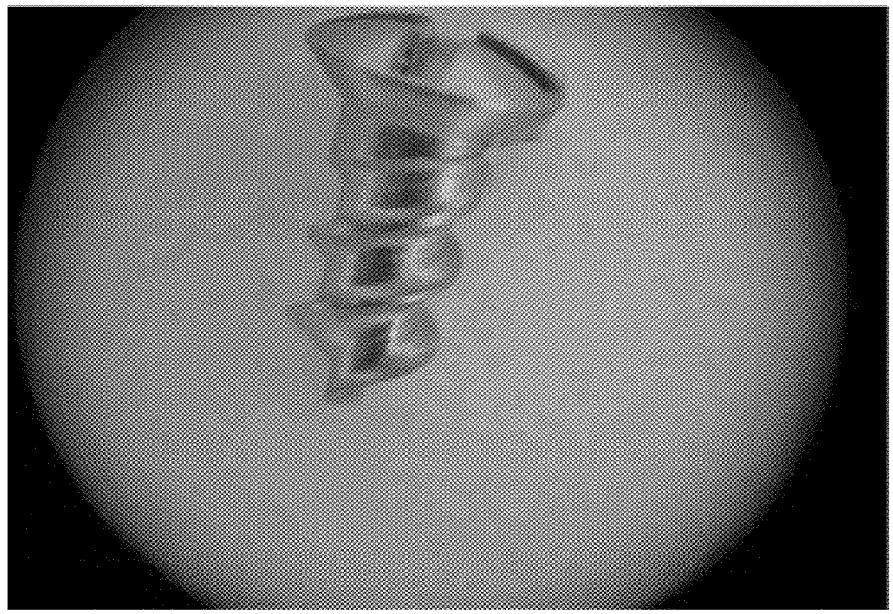
FIG. 5 is a photomicrograph of the bone screw of the present invention as depicted in FIG. 1.
Figure 6:
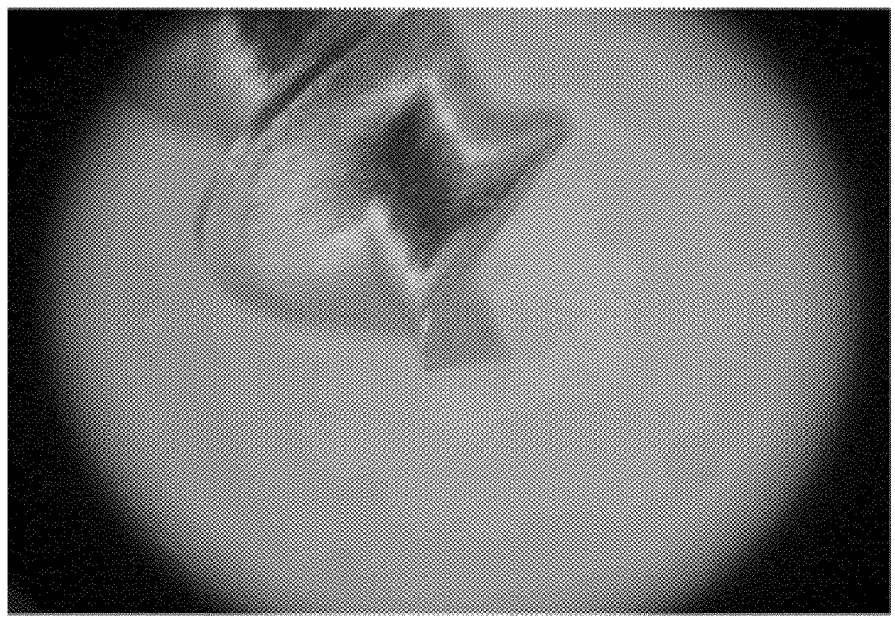
FIG. 6 is a photomicrograph of the cutting end of the bone screw of the present invention.
Figure 7:
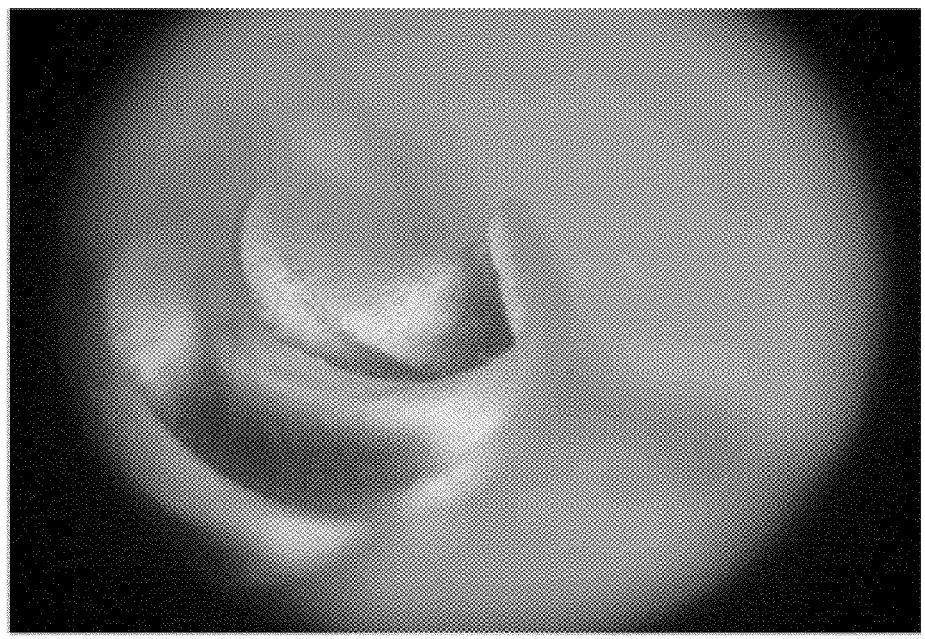
FIG. 7 is a photomicrograph of the cutting end of the bone screw of the present invention.

FIGS. 5-7 are photomicrographs of three perspectives of an exemplary bone screw according to the teachings of the present invention Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A bone screw comprising:
   a body including a longitudinal centerline;
   a cutting end including a flat rectangular cutting surface oriented perpendicularly to the longitudinal centerline; and
   a dual lead thread extending outwardly from the body in a spiral path from the cutting end and ending at a head located opposite the cutting end.

2. The bone screw of claim 1, wherein said dual lead thread is multi-pitched.

3. The bone screw of claim 1, wherein said dual lead thread is tapered towards the cutting end and transitions to a straight or slightly tapered thread towards the head.

4. The bone screw of claim 1, wherein the cutting end includes a first cutting edge which extends perpendicular from the longitudinal centerline to a first thread start point; and a second cutting edge which extends perpendicular from the longitudinal centerline to a second thread start point, the second cutting edge being parallel to the first cutting edge.

5. The bone screw of claim 1, wherein said bone screw is formed of a medical grade titanium alloy.

6. The bone screw of claim 1, wherein said bone screw is about 1.0 mm to about 5.0 mm in diameter.

7. The self-drilling bone screw of claim 1, wherein said bone screw is about 3.0 mm to about 100 mm in length.

8. The bone screw of claim 1, wherein the flat rectangular cutting surface is about 0.5 mm in length.

9. The bone screw of claim 1, wherein the flat rectangular cutting surface is about 0.1 mm in width.

10. A self-drilling bone screw comprising:
    a body including a longitudinal centerline;
    a cutting end including a flat rectangular cutting surface oriented perpendicularly to the longitudinal centerline; and
    a dual lead thread extending outwardly from the body in a spiral path from the cutting end and ending at a head.

11. The self-drilling bone screw of claim 10, wherein a pitch of a first thread and a second thread of the dual lead thread is tapered towards the cutting end.

12. The self-drilling bone screw of claim 11, wherein the pitch of the first thread and the second thread of the dual lead thread transitions to a straight or slightly tapered thread towards the head.

13. The self-drilling bone screw of claim 10, wherein said bone screw is formed of a medical grade titanium alloy.

14. The self-drilling bone screw of claim 10, wherein said bone screw is about 1.0 mm to about 5.0 mm in diameter.

15. The self-drilling bone screw of claim 10, wherein said bone screw is about 3.0 mm to about 100 mm in length.

16. The self-drilling bone screw of claim 10, wherein the flat rectangular cutting surface is about 0.5 mm in length.

17. The self-drilling bone screw of claim 10, wherein the flat rectangular cutting surface is about 0.1 mm in width.

18. A medical-grade surgical screw comprising:
    a head;
    a body including a longitudinal centerline;
    a cutting end including a flat rectangular cutting surface oriented perpendicularly to the longitudinal centerline; and
    a dual thread comprising a first thread originating from a first side of the flat rectangular cutting surface and a second thread originating from a second side, opposite the first side, of the flat rectangular cutting surface and wherein a pitch of the first thread and the second thread gradually decreases as the first thread and the second thread spiral from the cutting surface towards the head.

19. The medical-grade surgical screw of claim 18, wherein a length and a width of the flat rectangular cutting surface proportionally increases as a diameter of the body increases.

\* \* \* \* \*